United States Patent [19]

Ishihara et al.

[11] Patent Number: 5,000,881

[45] Date of Patent: Mar. 19, 1991

[54] POLYMERIZABLE ORGANOSILANE COMPOUND

[75] Inventors: Toshinobu Ishihara; Mikio Endo; Tohru Kubota, all of Niigata, Japan

[73] Assignee: Shin-Etsu Chemical Co., Ltd., Tokyo, Japan

[21] Appl. No.: 366,003

[22] Filed: Jun. 14, 1989

[30] Foreign Application Priority Data

Jun. 15, 1988 [JP] Japan ................. 63-147582

[51] Int. Cl.$^5$ ........................... C11C 3/00; C11C 3/04
[52] U.S. Cl. ........................... 260/410.9 N; 525/288; 525/308
[58] Field of Search ................. 260/410.9 N

[56] References Cited

U.S. PATENT DOCUMENTS 4,091,005  5/1978  Craig et al. ................. 260/410.9 N
4,724,100  2/1988  Gilbert et al. ............... 260/410.9 N Primary Examiner—Paul J. Killos
Assistant Examiner—Vera C. Clarke
Attorney, Agent, or Firm—Millen, White & Zelano

[57] ABSTRACT

A novel organosilane compound having polymerizability is disclosed which is a vinyl ω-triorganosilyl n-undecanoate of the formula $CH_2=CH-O-CO-(-CH_2-)_{10}-SiR_3$, in which R is an alkyl group having 1 to 4 carbon atoms, alkoxy group having 1 to 4 carbon atoms or trialkyl siloxy group of which the alkyl group has 1 to 4 carbon atoms. This compound can be prepared by the hydrosilylation reaction between a triorganosilane of the formula $HSiR_3$ and vinyl 10-undecenoate of the formula $$CH_2=CH-O-CO-(-CH_2-)_8-CH=CH_2$$

in the presence of a platinum catalyst. The compound is polymerizable to give not only a homopolymer of the compound alone but also a copolymer with other comonomers such as vinyl chloride, chloro trifluoroethylene, methyl methacrylate and the like.

4 Claims, 2 Drawing Sheets

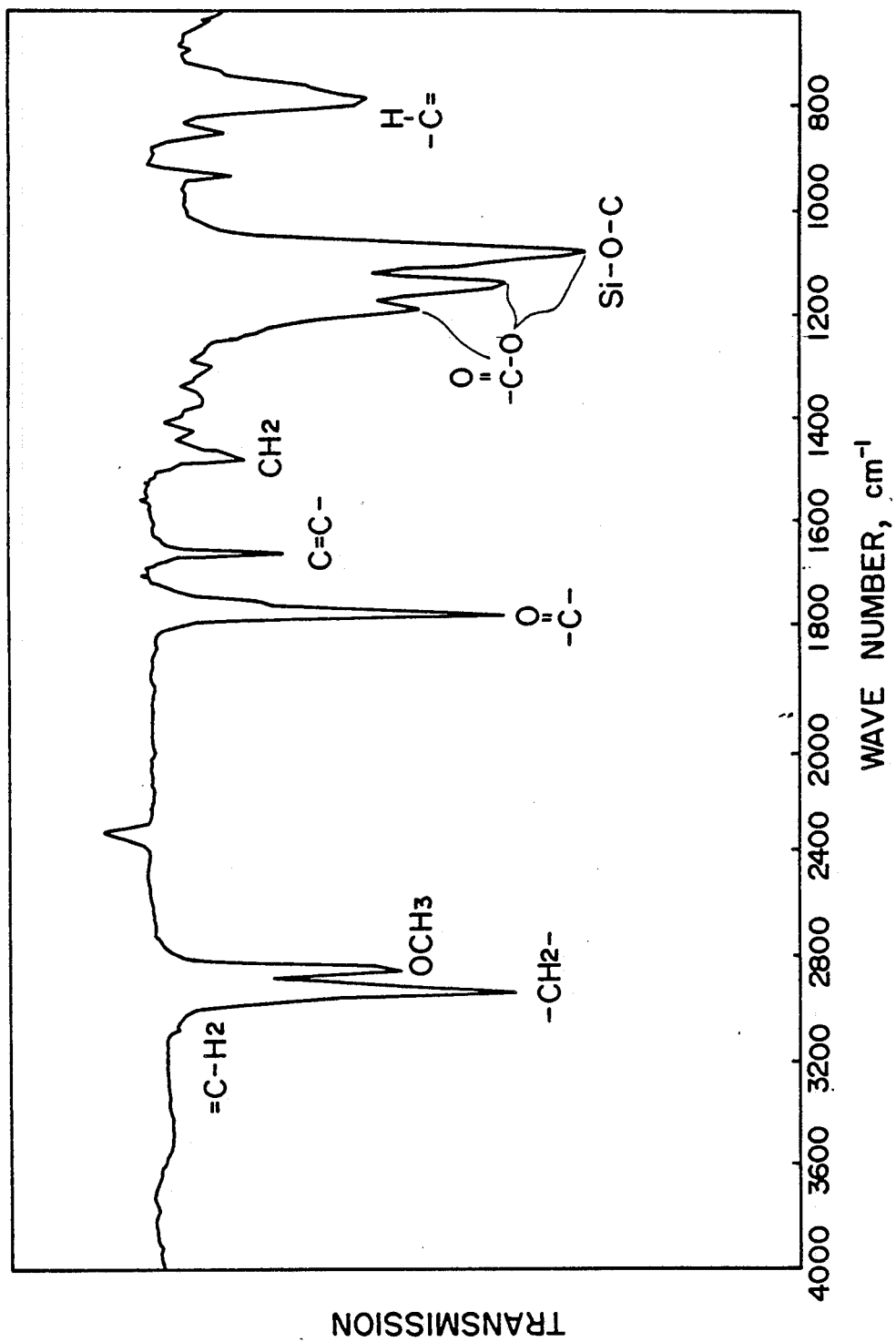
FIG. I

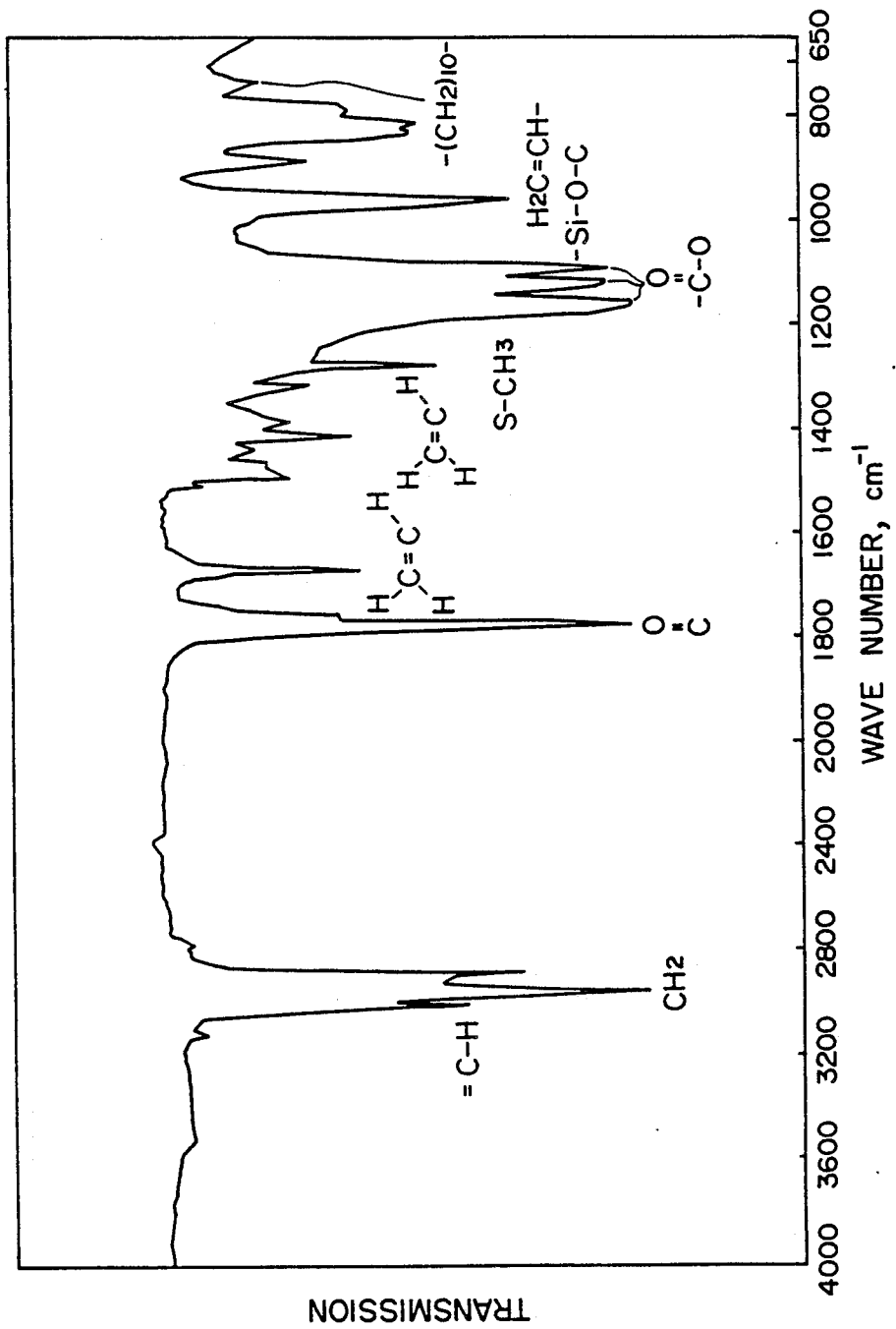

POLYMERIZABLE ORGANOSILANE COMPOUND

BACKGROUND OF THE INVENTION

The present invention relates to a novel organosilane compound not known in the prior art nor described in any literatures. More particularly, the invention relates to an organosilane compound in the form of a vinyl ester having polymerizability in homopolymerization and in copolymerization with one or more of other monomers and useful for the purpose of modification of various kinds of general-purpose synthetic resins or a material of gaspermeable membranes for oxygen enrichment. Further particularly, the invention relates to a vinyl ω-triorganosilyl n-undecanoate.

SUMMARY OF THE INVENTION

The novel polymerizable organosilane compound of the invention is a vinyl ω-triorganosilyl undecanoate represented by the general formula $$CH_2=CH-O-CO-(-CH_2-)_{10}-SiR_3. \qquad (I)$$

in which each R is a group selected from the class consisting of monovalent hydrocarbon groups having 1 to 4 carbon atoms such as methyl, ethyl, propyl, butyl and allyl groups, alkoxy groups having 1 to 4 carbon atoms such as methoxy, ethoxy, propoxy and butoxy groups and trialkylsiloxy groups of which each alkyl group has 1 to 4 carbon atoms such as trimethyl siloxy, triethyl siloxy, tripropyl siloxy and butyl dimethyl siloxy groups.

BRIEF DESCRIPTION OF THE DRAWING

FIGS. 1 and 2 are each an infrared absorption spectrum of vinyl ω-trimethylsilyl n-undecanoate and vinyl ω-(methyl diethoxy silyl) n-undecanoate prepared in Examples 1 and 2, respectively.

DETAILED DESCRIPTION OF THE PREFERRED EMBODIMENTS

As is described above, the novel polymerizable organosilane compound of the invention is a vinyl ω-triorgansilyl n-undecanoate represented by the general formula (I) given above. Several compounds are included in the class depending on the kind and combination of the groups denoted by R in the formula. Examples of the inventive compound in conformity with the general formula (I) and the definition of the symbol R include: vinyl ω-triethylsilyl n-undecanoate of the formula $CH_2=CH-O-CO-(-CH_2-)_{10}-Si(C_2H_5)_3$; vinyl ω-trimethoxysilyl n-undecanoate of the formula $CH_2=CH-O-CO-(-CH_2-)_{10}-Si(OCH_3)_3$; vinyl ω-(methyl diethoxy silyl) n-undecanoate of the formula $CH_2=CH-O-CO-(-CH_2-)_{10}Si(CH_3)(OC_2H_5)_2$; vinyl ω-tris(trimethyl siloxy)silyl n-undecanoate of the formula $CH_2=CH-O-CO-(-CH_2-)_{10}-Si[OSi(CH_3)_3]_3$ and the like. Needless to say, the scope of the present invention is not limited to these particular compounds.

The above described novel organosilane compound can be synthesized, for example, by the method described below. Thus, a hydrosilylation reaction is undertaken between vinyl 10-undecenoate of the formula $CH_2=CH-O-CO-(-CH_2-)_2-)_8-CH=CH_2$ and a triorganosilane compound of the formula $HSiR_3$, in which R has the same meaning as defined above, such as triethyl silane, trimethoxy silane, methyl diethoxy silane, tris(trimethyl siloxy) silane and the like in the presence of a catalytic amount of a platinum compound such as chloroplatinic acid. The reaction proceeds according to the following reaction equation:

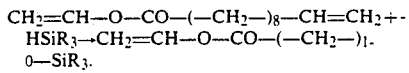

The reaction can proceed either without any solvent or in an organic solvent. Suitable organic solvents include ethers such as tetrahydrofuran and hydrocarbon solvents such as benzene and toluene. The reaction proceeds at a temperature in the range from 30° to 150° C. or, preferably, from 70° to 120° C.

The novel organosilane compound of the invention is a vinyl ester and has good polymerizability either alone or with other ethylenically unsaturated monomers such as vinyl chloride, chlorotrifluoroethylene, methyl methacrylate and the like to give a copolymer. Accordingly, the inventive polymerizable organosilane compound is useful as a modifying agent of various kinds of synthetic resins and also as a material of polymeric membranes for oxygen enrichment and crosslinkable resins.

In the following, the polymerizable organosilane compound of the invention is described in more detail by way of examples.

EXAMPLE 1

Into a four-necked flask of 500 ml capacity equipped with a stirrer, reflux condenser, thermometer and dropping funnel were introduced 210 g (1 mole) of vinyl 10-undecenoate, 0.1 g of 2,6-ditert-butyl p-cresol (BHT) and 0.43 g of a catalyst solution containing 2% by weight of platinum, which has been prepared by a heat treatment of a mixture of chloroplatinic acid and 2-ethylhexyl alcohol followed by stripping of hydrogen chloride, water and excessive amount of the 2-ethylhexyl alcohol, and the mixture in the flask was heated up to a temperature of 90° C. Thereafter, 122 g (1 mole) of trimethoxy silane were added dropwise to the flask through the dropping funnel so as to effect the reaction in the reaction mixture. After completion of the dropwise addition of the silane, the reaction mixture was heated at 110° C. for 5 hours to complete the reaction. The reaction mixture was then subjected to distillation under reduced pressure to give 279 g of a fraction boiling at 153° to 158° C. under a pressure of 1 mmHg and having a gaschromatographic purity of 98%. This product could be identified to be vinyl ω-trimethoxysilyl n-undecanoate from the analytical results shown below by the gas chromatographic-mass spectrometric analysis (GC-MS), nuclear magnetic resonance spectrometry (NMR) and infrared absorption spectrometry (IR). The above mentioned yield of the product was 82% of the theoretical value.

GC-MS: m/z (relative intensity of peaks) 289(71); 257(6); 219(5); 121(100); 107(10); 91(26); 55(13); 41(8)

NMR: δ(ppm)

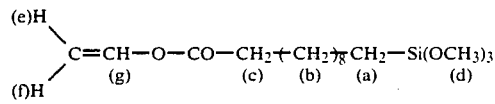

a: 0.5 ppm (T); b: 1.5 ppm (M); c: 2.54ppm (T); b: 3.7 ppm (S); e: 4.7 ppm (D); f: 5.0 ppm (D); g: 7.5 ppm (D)
IR: See FIG. 1.

EXAMPLE 2

The experimental procedure was substantially the same as in Example 1 excepting replacemtn of the trimethoxy silane with 134 g (1 mole) of methyl diethoxy silane to give 248 g of a fraction boiling at 157° C. under a reduced pressure of 2 mmHg and having a gas chromatographic purity of 97% . This product could be identified to be vinyl ω-(methyl diethoxy silyl) n-undecanoate from the analytical results of GC-MS, NMR and IR shown below. The above mentioned yield of the product was 70% of the theoretical value. GC-MS: m/z (relative intensity of peaks) 329(3); 301(38); 299(2); 231(8); 227(6); 133(100); 105 (16); 89(16); 77(16)
NMR: δ(ppm)

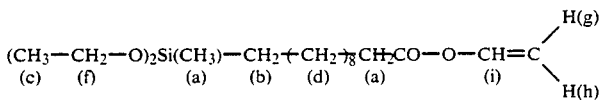

a: 0 ppm (S); b: 0.5 ppm (T); c: 1.11 ppm (T); d: 1.22 ppm (M); e: 2.25 ppm (t); f: 3.58 ppm (Q); g: 4.35 ppm (D); h: 4.65 ppm (D); i: 7.06 ppm (D)
IR: See FIG. 2.

What is claimed is:

1. A vinyl ω-(triorganosilyl) n-undecanoate represented by the formula $$CH_2=CH-O-CO-(-CH_2-)_{10}-SiR_3,$$

in which each R is a member of the group consisting of monovalent hydrocarbon groups of 1 to 4 carbon atoms, alkoxy groups of 1 to 4 carbon atoms and trialkyl siloxy groups of which each alkyl group is of 1 to 4 carbon atoms.

2. Vinyl ω-(trimethylsilyl) n-undecanoate.

3. Vinyl ω-(methyl diethoxy silyl) n-undecanoate.

4. A compound of claim 1 wherein at least one R is methyl.

* * * * *